(12) United States Patent
Delaney, Jr. et al.

(10) Patent No.: US 10,342,899 B2
(45) Date of Patent: Jul. 9, 2019

(54) BIOLOGICALLY INERT COATING FOR IMPLANTABLE MEDICAL DEVICES

(71) Applicant: Cardiac Pacemakers, Inc., St. Paul, MN (US)

(72) Inventors: Joseph T. Delaney, Jr., Minneapolis, MN (US); David R. Wulfman, Minneapolis, MN (US); Sarah M. Gruba, Vadnais Heights, MN (US); Michael J. Kane, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 281 days.

(21) Appl. No.: 15/382,712

(22) Filed: Dec. 18, 2016

(65) Prior Publication Data

US 2017/0173223 A1 Jun. 22, 2017

Related U.S. Application Data

(60) Provisional application No. 62/269,981, filed on Dec. 19, 2015.

(51) Int. Cl.
| | | |
|---|---|---|
| *A61L 27/34* | (2006.01) | |
| *A61L 31/10* | (2006.01) | |
| *C09D 165/04* | (2006.01) | |

(52) U.S. Cl.
CPC .............. *A61L 31/10* (2013.01); *A61L 27/34* (2013.01); *A61L 2420/02* (2013.01); *A61L 2420/08* (2013.01); *C09D 165/04* (2013.01)

(58) Field of Classification Search
CPC ...... A61L 2420/08; A61L 27/34; A61L 31/10; A61L 2420/02; A21L 2420/08
See application file for complete search history.

(56) References Cited

U.S. PATENT DOCUMENTS

| | | |
|---|---|---|
| 4,179,337 A | 12/1979 | Davis et al. |
| 5,488,954 A | 2/1996 | Sleva et al. |
| 6,451,003 B1 | 9/2002 | Prosl et al. |
| 6,555,157 B1 | 4/2003 | Hossainy |
| 6,617,027 B2 | 9/2003 | Kim et al. |
| 6,669,980 B2 | 12/2003 | Hansen |
| 6,793,960 B1 | 9/2004 | Michal et al. |
| 7,037,332 B2 | 5/2006 | Kutryk et al. |
| 7,322,965 B2 | 1/2008 | Gibson et al. |
| 7,329,366 B1 | 2/2008 | Gale et al. |
| 7,491,233 B1 | 2/2009 | Ding et al. |
| 7,591,841 B2 | 9/2009 | Hossainy et al. |
| 7,650,848 B2 | 1/2010 | Brennan et al. |
| 8,131,376 B1 | 3/2012 | Faraji et al. |
| 8,175,722 B2 | 5/2012 | Parker et al. |
| 8,263,107 B2 | 9/2012 | Pacetti et al. |
| 8,948,881 B2 | 2/2015 | Fisk |
| 2001/0008931 A1 | 7/2001 | Van Antwerp et al. |
| 2002/0019658 A1 | 2/2002 | Munshi |
| 2003/0104028 A1 | 6/2003 | Hossainy et al. |
| 2004/0044404 A1 | 3/2004 | Stucke et al. |
| 2004/0167633 A1 | 8/2004 | Wen et al. |
| 2006/0004432 A1 | 1/2006 | Parker et al. |
| 2006/0008500 A1 | 1/2006 | Chavan et al. |
| 2006/0057180 A1 | 3/2006 | Chilkoti et al. |
| 2007/0250045 A1 | 10/2007 | Trieu |
| 2008/0140152 A1 | 6/2008 | Imran et al. |
| 2008/0312356 A1 | 12/2008 | Kobrin et al. |
| 2009/0043369 A1 | 2/2009 | Radeloff |
| 2009/0093879 A1 | 4/2009 | Wawro et al. |
| 2009/0123516 A1 | 5/2009 | Agrawal et al. |
| 2009/0247666 A1* | 10/2009 | Yu ...................... A61L 24/0042 523/118 |
| 2010/0114225 A1 | 5/2010 | Imran et al. |
| 2010/0152708 A1 | 6/2010 | Li et al. |
| 2010/0198150 A1 | 8/2010 | Michal et al. |
| 2011/0257702 A1 | 10/2011 | Kara et al. |
| 2011/0306722 A1 | 12/2011 | Lellouche et al. |
| 2013/0029421 A1 | 1/2013 | Komvopoulos et al. |
| 2013/0098550 A1 | 4/2013 | Sargeant et al. |
| 2014/0114435 A1 | 4/2014 | Carpenter et al. |
| 2014/0172028 A1 | 6/2014 | Meredith |
| 2014/0316482 A1 | 10/2014 | Kane et al. |
| 2015/0283301 A1 | 10/2015 | Semetey et al. |
| 2016/0038743 A1 | 2/2016 | Foster et al. |

(Continued)

FOREIGN PATENT DOCUMENTS

| | | |
|---|---|---|
| CN | 103079462 A | 5/2013 |
| EP | 0633031 A1 | 1/1995 |
| JP | 2002505930 A | 2/2002 |

(Continued)

OTHER PUBLICATIONS

Golda et al, "Oxygen plasma functionalization of parylene C coating for implants surface: Nanotopography and active sites for drug anchoring", Materials Science and Engineering C 33 (2013) 4221-4227.

International Search Report and Written Opinion issued in PCT/US2016/067409, dated Mar. 29, 2017, 14 pages.

Tan et al., Surface Engineering and Patterning Using Parylene for Biological Applications, Materials 2010, 3, 1803-1832; doi: 10.3390/ma3031803; ISSN 1996-1944, www.mdpi.com/journal/materials.

International Preliminary Report on Patentability issued in PCT/US2016/067409, dated Jun. 28, 2018, 7 pages.

Barth, Andreas. "Review: The Infrared Absorption of Amino Acide Side Chains," Progress in Biophysics & Molecular Biology, 74:141-173, 2000.

(Continued)

*Primary Examiner* — Ramsey Zacharia
(74) *Attorney, Agent, or Firm* — Faegre Baker Daniels LLP

(57) ABSTRACT

A coating for an implantable medical device includes a poly(monochloro-p-xylylene) coating formed on at least a portion of the implantable medical device, and a layer including at least one of poly(ethylene glycol) and a poly(ethylene glycol) derivative linked to the poly(monochloro-p-xylylene) coating by covalent bonds.

15 Claims, 2 Drawing Sheets

(56) References Cited

U.S. PATENT DOCUMENTS

2018/0043056 A1     2/2018     Frankson et al.

FOREIGN PATENT DOCUMENTS

| | | |
|---|---|---|
| JP | 2005523116 A | 8/2005 |
| JP | 2010537728 A | 12/2010 |
| JP | 201363322 A | 4/2013 |
| WO | WO9307924 A1 | 4/1993 |
| WO | 1998017331 A1 | 4/1998 |
| WO | WO03072156 A1 | 9/2003 |
| WO | 2008006097 A2 | 1/2008 |
| WO | 2010001325 A2 | 1/2010 |
| WO | 2010057142 A2 | 5/2010 |
| WO | 2010094968 A2 | 8/2010 |
| WO | 2014041508 A1 | 3/2014 |
| WO | 2016025407 A1 | 2/2016 |

OTHER PUBLICATIONS

Grinstaff, Mark W. and Meyers, Steven R. "Biocompatible and Bioactive Surface Modifications for Prolonged in Vivo Efficacy." Chem. Rev., 112(3):1-37, Mar. 14, 2012.

International Search Report and Written Opinion issued in PCT/US2017/046160, dated Oct. 20, 2017, 15 pages.

Park, Ki Dong; et. al. "Bacterial Adhesion on PEG Modified Polyurethane Surfaces." Biomaterials, 19:851-859, 1998.

Patel, Shyam; et. al. "Control of Cell Adhesion on Poly(methyl methacrylate)." Biomaterials, 27:2890-2897, 2006.

Xiao, Shou-Jun, et al. "Covalent Attachment of Cell-Adhesive, (Arg-Gly-Asp)-Containing Peptides to Titanium Surfaces." Langmuir 14:5507-5516, 1998.

Abdallah, H.I., et al., "Pacemaker contact sensitivity: clinical recognition and management", Ann Thorac Surg., 57 (4) Apr. 1994, pp. 1017-1018.

Au, Sam H., et al. "A New Angle on Pluronic Additives: Advancing Droplets and Understanding in Digital Microfluidics." Langmuir, 27:8586-8594, 2011.

Bain, Colin et al., "Formation of monolayer films by the spontaneous assembly of organic thiols from solution onto gold", J. Am. Chem. Soc., 111(1), 1989, pp. 321-335.

Benhabbour, Soumya et al., "Cell adhesion and proliferation on hydrophilic dendritically modified surfaces", Biomaterials, 29, (2008), pp. 4177-4186.

Berger, Manuel. "Biosensors Coated With Sulfated Polysaccharides for the Detection of Hepatocyte Growth Fatctor/Scatter Factor in Cell Culture Medium." Biosensors and Bioelectronics, 26:1706-1709, 2010.

Ferringer, T., et al., "Telangiectatic erythematous cutaneous reaction to an implantable cardioverter defibrillator", Am J Contact Dermat., 14(1), (Mar. 2003), pp. 37-40.

Harder, P, et al., "Molecular Conformation in Oligo(ethylene glycol)-Terminated Self-Assembled Monolayers on Gold and Silver Surfaces Determines their Ability to Resist Protein Adsorption", J. Phys. Chem. B, 102, (1998), pp. 426-436.

Herrwerth, Sascha et al., "Factors that Determine the Protein Resistance of Oligoether Self-Assembled Monolayers—Internal Hydrophilicity, Terminal Hydrophilicity, and Lateral Packing Density", J. Am. Chem. Soc., 125, (2003), pp. 9359-9366.

Howard, Melissa, et al., "PEGylation of Nanocarrier Drug Delivery Systems: State of the Art", J. Biomed. Nanotechnol. 4, (2008), pp. 133-148.

International Preliminary Report on Patentability issued in PCT/US2015/044525, dated Feb. 23, 2017, 8 pages.

International Search Report and Written Opinion issued in PCT/US2015/015336, dated Jul. 10, 2015, 14 pages.

International Search Report and Written Opinion issued in PCT/US2015/044525, dated Oct. 9, 2015, 10 pages.

Lin, Shaohui et al., "Antifouling Poly(Beta-Peptoid)s", Biomacromolecules, 12(7), (2011), pp. 2473-2582.

Ma, Hongwei et al., ""Non-Fouling" Oligo(ethylene glycol)-Functionalized Polymer Brushes Synthesized by Surface-Initiated Atom Transfer Radical Polymerization", Advanced Materials, 2004, 16(4), (Feb. 17, 2004), pp. 338-341.

Ma, Hongwei, et al., "Surface-Initiated Atom Transfer Radical Polymerizatino of Oligo9ethylene glycol) Methyl Methacrylate from a Mixed Self-Assembled Monolayer on Gold", Advanced Functional Materials, 16, (2006), pp. 640-648.

Maeda, Hatsuo, et al., "Electrochemical Coating with Poly(phenylene oxide) Films Bearing Oligoether Groups as a Tool for Elimination of Protein Adsorption to Electron Surfaces", Analytical Sciences, 15, (Jul. 1999), pp. 633-639.

Mrksich, Using Self-Assembled Monolayers to Understand the Interactions of Man-Made Surfaces with Proteins and Cells, Annual Reviews Biophys. Biomol. Struct. (1996) 25, pp. 55-78.

Needham, D., et al., "Polymer-Grafted Liposomes: Physical Basis for the Stealth" Property:, Journal of Liposome Research, 2(3), (1992), pp. 411-430.

Niebauer, M. J., et al., "Iridium oxide-coated defibrillation electrode: reduced shock polarization and improved defibrillation efficacy", Circulation, 96(10), (Nov. 18, 1997), pp. 3732-3736.

Orner, Brendan P. et al., "Arrays for the combinatorial Exploration of Cell Adhesion", J. Am. Chem. Soc., 126, (Aug. 14, 2004), pp. 10808-10809.

Pale-Grosdemange, Formation of Self-Assembled Monolayers by Chemisorption of Derivatives of Oligo(ethylene glycol) of Structure HS(CH2)11(OCH2CH2)mOH on Gold, Journal of American Chemical Society, vol. 113, No. 1, (1991), pp. 12-20.

Pensa, Evangelina et al., "The Chemistry of the SulfurGold Interface: In Search of a Unified Model", Accounts of Chemical Research, 45(8), (2012), pp. 1183-1192.

Singh, Nripen et al., "The role of independently variable grafting density and layer thickness of polymer nanolayers on peptide adsorption and cell adhesion", Biomaterials, 28, (2007), pp. 763-771.

Skoet, R. et al., "Epoxy Contact Dermititis due to Pacemaker Compounds", Cardiology, 99, (2003), 112.

Stouffer, Jan M. et al., "Polymer monolayers prepared by the spontaneous adsorption of sulfur-functionalized polystyrene on gold surfaces", Macromolecules, 21(5), (1988), pp. 1204-1208.

Su, Chiao-Tzu, et al. "A Facile Approach Toward Protein-Resistant Biointerfaces Based on Photodefinable Poly-P-Xylylene Coating." Colloids and Surfaces B: Biointerfaces, 116:727-733, 2014.

Syburra, T. et al., "Gold-coated pacemaker implantation after allergic reactions to pacemaker compounds", Europace, 12(5), (May 2010), pp. 749-750.

Takae, Seiji et al., "Ligand density effect on biorecognition by PEGylated gold nanoparticles: regulated interaction of RCA 120 lectin with lactose installed to the distal end of tethered PEG strands on gold surface", Biomacromolecules, 6 (2), (2005), pp. 818-824.

Terrill, Roger H. et al., "Structural Evolution of Hexadecanethiol Monolayers on Gold during Assembly: Substrate and Concentration Dependence of Monolayer Structure and Crystallinity", Langmuir, 14, (1998), pp. 845-854.

Tsai, Meng-Yu, et al. "Vapor-Based Multicomponent Coatings for Antifouling and Biofunctional Synergic Modifications." Adv. Funct. Mater., 24:2281-2287, 2014.

Vanderah, David J., et al. "Characterization of a Series of Self-Assembled Monolayers of Alkylated 1-Thiaologo ethylene oxides) 4-8 on Gold." Langmuir 16:6527-6532, 2000.

Vanderah, David J., et al. "Self-Assembled Monolayers of Methyl 1-Thiahexa(ethylene oxide) for the Inhibition of Protein Adsorption." Langmuir 18:4674-4680, 2002.

Vanderah, David J., et al. "Synthesis and Characterization of Self-Assembled Monolayers of Alkylated 1-Thiahexa (ethylene oxide) Compounds on Gold." Langmuir 14:6919-6923, 1998.

Veiseh, Mandana et al., "Guided cell patterning on gold-silicon dioxide substrates by surface molecular engineering", Biomaterials, 25, (2004), pp. 3315-3324.

Vos, Johannes G. et al., "Formation and Characterization of Modified Surfaces", Supramolecular Assemblies, John Wiley & Sons, Ltd., (2003), pp. 87-152.

(56) References Cited

OTHER PUBLICATIONS

Zhu, B. et al., "Chain-length dependence of the protein and cell resistance of oligo(ethylene glycol)-terminated self-assembled monolayers on gold", J Biomed Mater Res., 56(3), (Sep. 5, 2001), pp. 406-416.

Buxadera-Palomero et al., "Antifouling coatings for dental implants: Polyethylene glycol-like coatings on titanium by plasma polymerization", Biointerphases, vol. 10, No. 2, Jun. 2015' pp. 029505-1 to 029505-11.

Hamilton, Douglas W., et al, "Comparison of the Response of Cultured Osteoblasts and Osteoblasts Outgrown From Rat Calvarial Bone Chips to Nonfouling KRSR and FHRRIKA-Peptide Modified Rough Titanium Surfaces." Research Gate, Journal of Biomedical Materials Research Part B Applied Biomaterials, pp. 517-527, Nov. 2009.

Harris et al., "*Staphylococcus aureus* adhesion to titanium oxide surfaces coated with non-functionalized and peptide-functionalized poly(l-lysine)-grafted-poly(ethylene glycol) copolymers", Biomaterials, vol. 25, No. 18, Aug. 2004, pp. 4135-4148.

Hyukjin Lee et al., "Catechol-Grafted Poly(ethylene glycol) for PEGylation on Versatile Substrates", Languir, vol. 26, No. 6, Mar. 16, 2010, pp. 3790-3793.

International Search Report and Written Opinion issued in PCT/US2017/037697, dated Aug. 28, 2017, 13 pages.

Norma A. Alcantar et al., Polyethylene glycol-coated biocompatible surfaces:, Journal of Biomedical Materials Research, vol. 51, No. 3, Sep. 5, 2000, pp. 343-351.

Olivares-Navarrete, Rene. "Osteoblasts Exhibit a More Differentiated Phenotype and Increased Bone Morphogenetic Protein Production on Titanium Alloy Substrates Than on Poly-Ether-Ether-Ketone." The Spine Journal, 12:265-272, 2012.

Reddy, Shravanthi T., et al. "Micropatterned Surfaces for Reducing the Risk of Catheter-Associated Urinary Tract Infection: An In Vitro Study on the Effect of Sharklet Micropatterned Surfaces to Inhibit Bacterial Colonization and Migration of Uropathogenic *Escherichia coli*." Journal of Endourology, 25(9):1547-1552, Sep. 2011.

Scardino, Andrew J. "Mini Review: Biomimetic Models and Bioinspired for Fouling Control." Biofouling, 27(1):73-86, Jan. 2011.

Schwartz, Zvi, et al. "RGD-Containing Peptide GCRGYGRGDSPG Reduces Enhancement of Osteoblast Differentiation by Poly(L-Lysine)-Graft-Poly(ethylene glycol)-Coated Titanium Surfaces." ResearchGate, Journal of Biomedical Materials Research Part A, pp. 458-472, Mar. 2004.

Takao Hanawa, "A comprehensive review of techniques for biofunctionalization of titanium", Journal of Periodontal & Implant Science, vol. 41, No. 6, pp. 262-272, Jan. 2011.

\* cited by examiner

BIOLOGICALLY INERT COATING FOR IMPLANTABLE MEDICAL DEVICES

CROSS-REFERENCE TO RELATED APPLICATION

This application claims priority to Provisional Application No. 62/269,981, filed Dec. 19, 2015, which is herein incorporated by reference in its entirety.

TECHNICAL FIELD

The present invention relates to coatings and methods for coating implantable medical devices. More specifically, the invention relates to biologically inert coatings and methods for producing biologically inert coatings for implantable medical devices.

BACKGROUND

Medical devices implanted into a body may be designed such that the device interacts with the body and produces a response, for example, to cause tissue growth around a portion of the medical device to secure the medical device in place. In some implantable medical devices, it is desirable for only a portion of the device to interact with the body. For example, a leadless cardiac pacemaker (LCP) is a medical device implanted into a ventricle of a heart to provide electrophysiological therapy to the heart. The LCP is contained entirely within the ventricle. The LCP is self-contained and includes a control systems and a battery so that no leads into the heart are necessary for power or control. The LCP may include tines at a distal end that are designed to interact with the body to produce a tissue growth response around the tines to secure the LCP to the endocardium. It is desirable that the remainder of the external surface of the LCP not interact with the body so that tissue growth is confined to the tines at the distal end. Limiting the tissue growth in this way makes it easier to remove the LCP once the battery becomes depleted.

What is needed is a reliably biologically inert coating that can be formed on the exterior surface of at least a portion of an implantable device to limit interaction with the body and the growth of tissue.

SUMMARY

Example 1 is a coating for an implantable medical device. The coating includes a poly(monochloro-p-xylylene) coating formed on at least a portion of the implantable medical device, and a layer including at least one of poly(ethylene glycol) and a poly(ethylene glycol) derivative linked to the poly(monochloro-p-xylylene) coating by covalent bonds.

In Example 2, the coating of Example 1, wherein the layer including at least one of poly(ethylene glycol) and a poly(ethylene glycol) derivative is a monolayer.

In Example 3, the coating of either of Examples 1 or 2, wherein the layer including at least one of poly(ethylene glycol) and a poly(ethylene glycol) derivative is covalently bonded directly to the poly(monochloro-p-xylylene) coating.

In Example 4, the coating of any of Examples 1-3, wherein the layer including at least one of poly(ethylene glycol) and a poly(ethylene glycol) derivative includes poly(ethylene glycol) or methoxy poly(ethylene glycol) glycidyl ether.

In Example 5, the coating of Example 1, further including bifunctional linker disposed between poly(monochloro-p-xylylene) coating and the layer including at least one of poly(ethylene glycol) and a poly(ethylene glycol) derivative, wherein the bifunctional linker is covalently bonded to the poly(monochloro-p-xylylene) coating and to the layer including at least one of poly(ethylene glycol) and a poly(ethylene glycol) derivative.

In Example 6, the coating of Example 5, wherein the layer including at least one of poly(ethylene glycol) and a poly(ethylene glycol) derivative includes poly(ethylene glycol) methyl ether.

In Example 7, the coating of either of Examples 5 or 6, wherein the bifunctional linker includes a diisocyanate.

In Example 8, the coating of either of Examples 5 or 6, wherein the bifunctional linker includes (3-glycidyloxypropyl)trimethoxysilane.

Example 9 is an implantable medical device including an exterior surface, and a coating according to any of Examples 1-8 disposed on at least a portion of the exterior surface.

Example 10 is a method for coating an implantable medical device. The method includes forming a coating of poly(monochloro-p-xylylene) on at least a portion of the implantable medical device, activating a surface of the poly(monochloro-p-xylylene) coating by forming hydroxyl groups on the surface, and treating the activated surface with at least one of a poly(ethylene glycol) and a poly(ethylene glycol) derivative to link the at least one of a poly(ethylene glycol) and a poly(ethylene glycol) derivative to the poly(monochloro-p-xylylene) coating by covalent bonds.

In Example 11, the method of Example 10, wherein activating the surface of the layer of poly(monochloro-p-xylylene) includes treating the surface with an oxygen-containing plasma.

In Example 12, the method of either of Examples 10 or 11, wherein the at least one of a poly(ethylene glycol) and a poly(ethylene glycol) derivative includes poly(ethylene glycol) or methoxy poly(ethylene glycol).

In Example 13, the method of either of Examples 10 or 11, wherein treating the activated surface further includes treating the activated surface with a bifunctional linker, forming a monolayer of the bifunctional linker covalently bonded to the surface before treating the monolayer of the bifunctional linker with the at least one of a poly(ethylene glycol) and a poly(ethylene glycol) derivative, forming a monolayer of the at least one of a poly(ethylene glycol) and a poly(ethylene glycol) derivative covalently bonded to the monolayer of the bifunctional linker.

In Example 14, the method of Example 13, wherein the at least one of a poly(ethylene glycol) and a poly(ethylene glycol) derivative includes poly(ethylene glycol) methyl ether.

In Example 15, the method of either of Examples 13 or 14, wherein the bifunctional linker includes a diisocyanate.

Example 16 is a coating for an implantable medical device. The coating includes a poly(monochloro-p-xylylene) coating formed on at least a portion of the implantable medical device, and monolayer including at least one of poly(ethylene glycol) and a poly(ethylene glycol) derivative linked to the poly(monochloro-p-xylylene) coating by covalent bonds.

In Example 17, the coating of Example 16, wherein the monolayer including at least one of poly(ethylene glycol) and a poly(ethylene glycol) derivative is covalently bonded directly to the poly(monochloro-p-xylylene) coating.

In Example 18, the coating of Example 17, wherein the monolayer including at least one of poly(ethylene glycol) and a poly(ethylene glycol) derivative includes poly(ethylene glycol).

In Example 19, the coating of Example 17, wherein the monolayer including at least one of poly(ethylene glycol) and a poly(ethylene glycol) derivative includes methoxy poly(ethylene glycol).

In Example 20, the coating of any of Examples 16-19, wherein an average molecular weight of the at least one of the poly(ethylene glycol) and a poly(ethylene glycol) derivative is between about 200 grams per mole and about 20,000 grams per mole.

In Example 21, the coating of any of Examples 16-20, further including a bifunctional linker disposed between the poly(monochloro-p-xylylene) coating and the monolayer including at least one of poly(ethylene glycol) and a poly(ethylene glycol) derivative, wherein the bifunctional linker is covalently bonded to the poly(monochloro-p-xylylene) coating and to the monolayer including at least one of poly(ethylene glycol) and a poly(ethylene glycol) derivative.

In Example 22, the coating of Example 20, wherein the monolayer including at least one of poly(ethylene glycol) and a poly(ethylene glycol) derivative includes poly(ethylene glycol) methyl ether.

In Example 23, the coating of either of Examples 20 or 21, wherein the bifunctional linker includes a diisocyanate.

In Example 24, the coating of either of Examples 20 or 21, wherein the bifunctional linker includes (3-glycidyloxypropyl)trimethoxysilane.

Example 25 is an implantable medical device. The implantable medical device includes an exterior surface, and a coating disposed on at least a portion of the exterior surface. The coating includes a poly(monochloro-p-xylylene) coating formed on at least a portion of the implantable medical device, and a monolayer including at least one of poly(ethylene glycol) and a poly(ethylene glycol) derivative linked to the poly(monochloro-p-xylylene) coating by covalent bonds.

Example 26 is a method for coating an implantable medical device. The method includes forming a coating of poly(monochloro-p-xylylene) on at least a portion of the implantable medical device, activating a surface of the poly(monochloro-p-xylylene) coating by forming hydroxyl groups on the surface, and treating the activated surface with at least one of a poly(ethylene glycol) and a poly(ethylene glycol) derivative to link the at least one of a poly(ethylene glycol) and a poly(ethylene glycol) derivative to the poly(monochloro-p-xylylene) coating by covalent bonds.

In Example 27, the method of Example 26, wherein activating the surface of the layer of poly(monochloro-p-xylylene) includes treating the surface with an oxygen-containing plasma.

In Example 28, the method of Example 26, wherein activating the surface of the layer of poly(monochloro-p-xylylene) includes treating the surface with ultraviolet light in an oxygen-containing atmosphere.

In Example 29, the method of any of Examples 26-28, wherein the at least one of a poly(ethylene glycol) and a poly(ethylene glycol) derivative includes poly(ethylene glycol).

In Example 30, the method of any of Examples 26-28, wherein the at least one of a poly(ethylene glycol) and a poly(ethylene glycol) derivative includes methoxy poly(ethylene glycol).

In Example 31, the method of Example 26, wherein treating the activated surface further includes treating the activated surface with a bifunctional linker, forming a monolayer of the bifunctional linker covalently bonded to the surface before treating the monolayer of the bifunctional linker with the at least one of a poly(ethylene glycol) and a poly(ethylene glycol) derivative, forming a monolayer of the at least one of a poly(ethylene glycol) and a poly(ethylene glycol) derivative covalently bonded to the monolayer of the bifunctional linker.

In Example 32, the method of Example 31, wherein the at least one of a poly(ethylene glycol) and a poly(ethylene glycol) derivative includes poly(ethylene glycol) methyl ether.

In Example 33, the method of either of Examples 31-32, wherein the bifunctional linker includes a diisocyanate.

In Example 34, the method of Example 33, wherein the diisocyanate is 4,4'-methylenebis(phenyl isocyanate).

In Example 35, the method of either of Examples 31-32, wherein the bifunctional linker includes (3-glycidyloxypropyl)trimethoxysilane While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
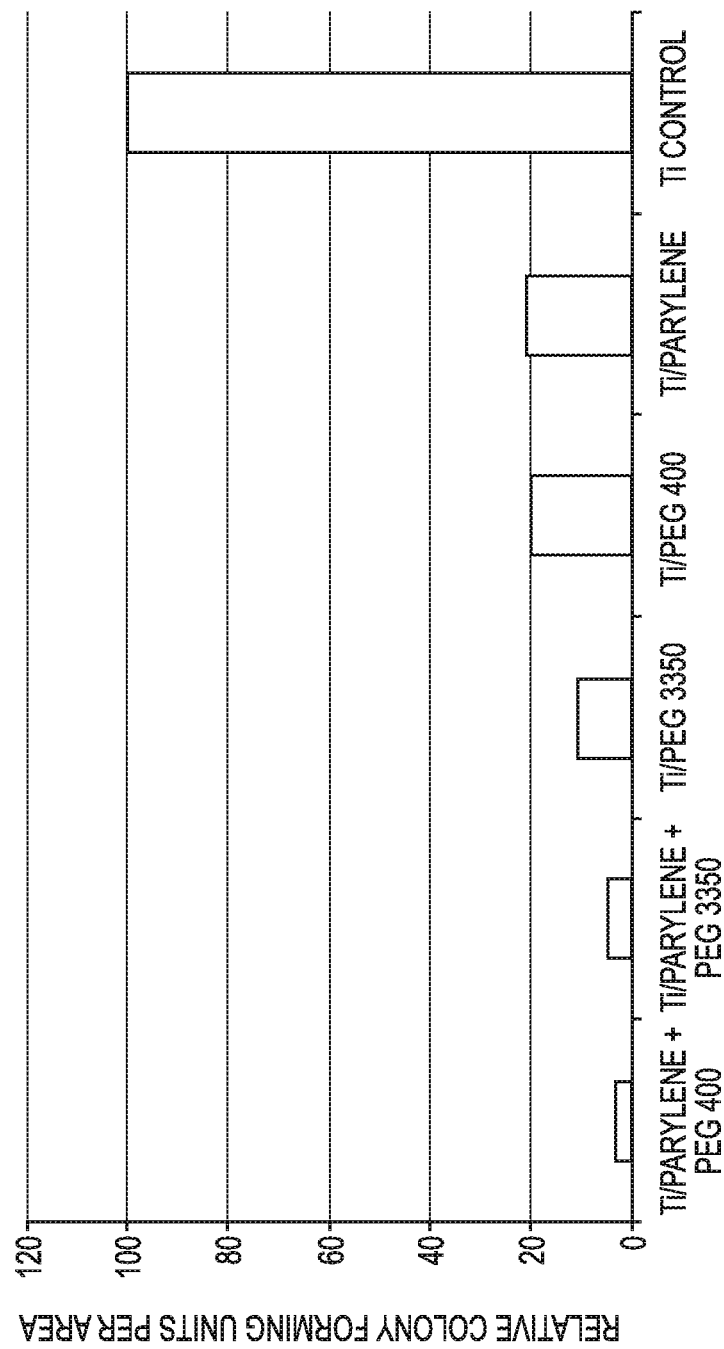
FIG. 1 is a graph of relative colony forming units over a predetermined area in accordance with embodiments of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The polymer poly(monochloro-p-xylylene), also known as parylene C, is often used as a coating for implantable medical devices. Poly(monochloro-p-xylylene) is deposited on a device surface from a vapor phase, resulting in a thin, conformal, pin-hole free polymer coating. Poly(monochloro-p-xylylene) is good moisture and chemical barrier, in addition to being a good dielectric barrier. These properties, among others, make parylene C particularly useful for use as a coating on all or part of an exterior surface of a leadless cardiac pacemaker (LCP).

Embodiments of the disclosure form an immobilized monolayer of poly(ethylene glycol) or a poly(ethylene glycol) derivative linked by covalent bonds to the poly(monochloro-p-xylylene) coating on a surface, such as an exterior surface, of an implantable medical device. The resulting coating is a biologically inert coating that can be formed on the exterior surface of at least a portion of an implantable device to limit interaction with tissue ingrowth and protein adsorption. A biologically inert coating can serve to limit attachment of platelets, which could otherwise lead to the development of a thrombosis.

In some embodiments, the poly(ethylene glycol) or the poly(ethylene glycol) derivative is covalently bonded directly to the poly(monochloro-p-xylylene) coating. In other embodiments, a bifunctional linker is covalently bonded to the poly(monochloro-p-xylylene) coating, and the poly(ethylene glycol) or the poly(ethylene glycol) derivative is covalently bonded to the bifunctional linker. The poly(ethylene glycol) or the poly(ethylene glycol) derivative monolayer presents an exterior surface that is biologically inert. Additionally, the poly(ethylene glycol) or the poly(ethylene glycol) derivative monolayer is durable and immobilized because it is linked to the poly(monochloro-p-xylylene) coating by covalent bonds.

In some embodiments in which the poly(ethylene glycol) or the poly(ethylene glycol) derivative is covalently bonded directly to the poly(monochloro-p-xylylene) coating, the poly(monochloro-p-xylylene) coating is formed on an exterior surface of an implantable medical device, the surface of the poly(monochloro-p-xylylene) coating is oxidatively activated, and the activated surface is treated directly with poly(ethylene glycol) or a poly(ethylene glycol) derivative. For example, the poly(monochloro-p-xylylene) coating may be deposited on the substrate by any suitable process, such as, but not limited to, vapor deposition. The vapor deposition of the poly(monochloro-p-xylylene) may include sublimation of dichloro-[2,2]-paracyclophane dimer, pyrolization of the dimer to form a monomer, and condensation of the monomer onto the exterior surface of the implantable medical device, as is known in the art.

Next, the surface of the poly(monochloro-p-xylylene) coating may be oxidatively activated to form hydroxyl functional groups at the surface, as shown in Equation 1 below:

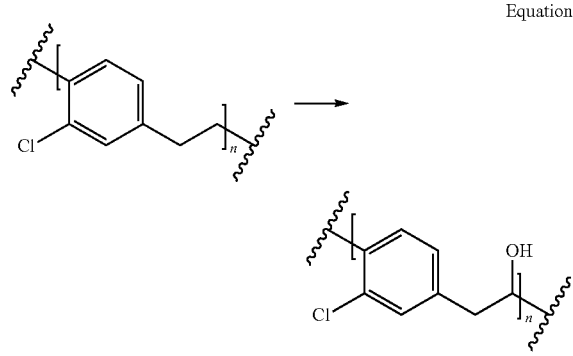

Equation 1

The surface may be activated by exposure to an oxygen-containing plasma, such as an oxygen plasma or a water plasma. A suitable exposure time provides sufficient time to form hydroxyl groups on the surface but does not significantly degrade the poly(monochloro-p-xylylene) coating. For example, the poly(monochloro-p-xylylene) coating may be exposed to an oxygen plasma for as little as about 1 second or as long as about 90 seconds. Alternatively, the surface may be activated by exposure to ultraviolet radiation in the presence of an oxygen-containing gas or vapor. Although Equation 1 shows the hydroxyl group formed at a methylene group, it is understood that the hydroxyl group may also form at any of the carbon atoms on the aromatic ring having two hydrogen atoms.

In some embodiments, following activation of the poly(monochloro-p-xylylene) coating, the activated surface is treated directly with poly(ethylene glycol) or a poly(ethylene glycol) derivative. In some embodiments, the activated poly(monochloro-p-xylylene) coating may be treated by dipping medical device in the poly(ethylene glycol) or the poly(ethylene glycol) derivative. In other embodiments, the activated poly(monochloro-p-xylylene) coating may be treated by spraying the poly(ethylene glycol) or the poly(ethylene glycol) derivative on to the medical device. Other suitable techniques include inkjet printing, roll coating, screen printing, and microcontact, stamping/contact printing the poly(ethylene glycol) or the poly(ethylene glycol) derivative on to the activated poly(monochloro-p-xylylene) coating on the medical device.

In some embodiments, the activated poly(monochloro-p-xylylene) coating is treated with poly(ethylene glycol) as shown in Equation 2 below:

Equation 2

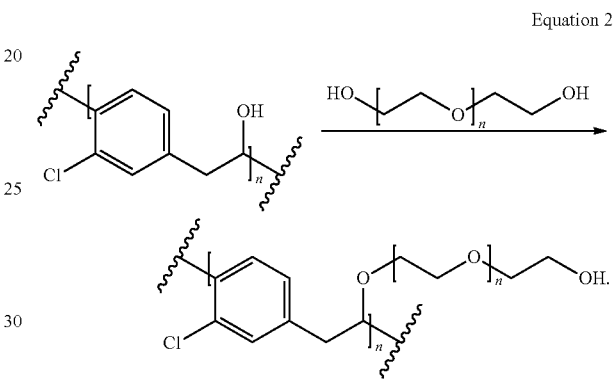

The result is a monolayer of poly(ethylene glycol) covalently bonded to the poly(monochloro-p-xylylene) coating by an ether linkage. The poly(ethylene glycol) monolayer is durable because it is linked to the poly(monochloro-p-xylylene) coating by covalent bonds. The poly(ethylene glycol) monolayer resists cracking or peeling from the poly(monochloro-p-xylylene) coating. The resulting coating provides a reliably biologically inert surface for the implantable medical device.

In other embodiments, the activated poly(monochloro-p-xylylene) coating is treated with a poly(ethylene glycol) derivative, such as methoxy poly(ethylene glycol) glycidyl ether as shown in Equation 3 below:

Equation 3:

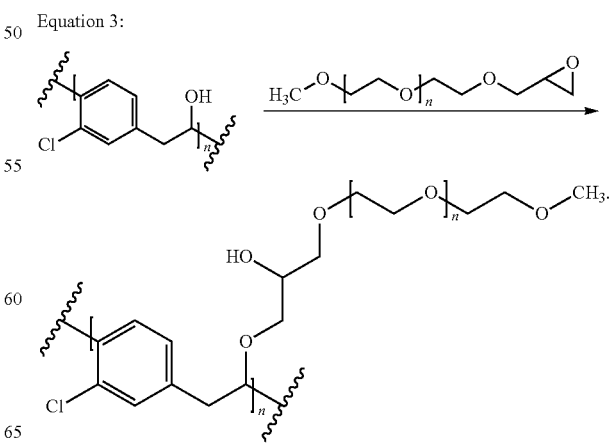

The result is a monolayer of methoxy poly(ethylene glycol) glycidyl ether covalently bonded to the poly(monochloro-p-xylylene) coating by an ether linkage. The methoxy poly(ethylene glycol) glycidyl ether monolayer is durable and immobilized because it is linked to the poly(monochloro-p-xylylene) coating by covalent bonds. The methoxy poly(ethylene glycol) glycidyl ether monolayer resists cracking or peeling from the poly(monochloro-p-xylylene) coating. The resulting coating provides a reliably biologically inert surface for the implantable medical device.

The hydroxyl groups formed during surface activation are in a high energy, highly reactive state and begin undesired reactions with other hydroxyl groups once the medical device is removed from the oxygen-containing plasma (or ultraviolet radiation). Reacted hydroxyl groups are unavailable to form covalent bonds during the treatment step. Thus, in some embodiments, the activated surface is treated with poly(ethylene glycol) or a poly(ethylene glycol) derivative within about 60 minutes of removal of the medical device from the oxygen-containing plasma (or ultraviolet radiation). In other embodiments, the activated surface is treated within about 50 minutes, about 40 minutes, about 30 minutes, about 20 minutes, or within about 10 minutes of removal of the medical device from the oxygen-containing plasma (or ultraviolet radiation).

As described herein, in other embodiments, a bifunctional linker is covalently bonded to the poly(monochloro-p-xylylene) coating, and the poly(ethylene glycol) or the poly(ethylene glycol) derivative is covalently bonded to the bifunctional linker. In such embodiments, the poly(monochloro-p-xylylene) coating can be formed on an exterior surface of an implantable medical device, and the surface of the poly(monochloro-p-xylylene) coating can be oxidatively activated as described above. Following activation of the surface, the surface may be treated with a bifunctional linker to form a monolayer of the bifunctional linker, and the monolayer of the bifunctional linker may then be treated with poly(ethylene glycol) or a poly(ethylene glycol) derivative as described above.

In some embodiments, the activated poly(monochloro-p-xylylene) coating may be treated by dipping medical device in the bifunctional linker. In other embodiments, the activated poly(monochloro-p-xylylene) coating may be treated by spraying the bifunctional linker on to the medical device. Other suitable techniques include inkjet printing, roll coating, screen printing, and microcontact, stamping/contact printing the bifunctional linker on to the activated poly(monochloro-p-xylylene) coating on the medical device.

Bifunctional linkers are molecules able to react on one end with hydroxyl functional groups of the activated poly(monochloro-p-xylylene) coating and react on another end with available end groups of the poly(ethylene glycol) or the poly(ethylene glycol) derivative. In the case where the poly(ethylene glycol) derivative is hydroxyl terminated, suitable bifunctional linkers include diisocyanate and (3-glycidyloxypropyl)trimethoxysilane. Other suitable bifunctional linkers include bis-epoxy functionalized molecules such as bisphenol A diglycidyl ether (BADGE), bisphenol AF, and bisphenol S. Poly(ethylene glycol) chains functionalized with reactive end groups may also be used as bifunctional linkers, for example, epoxy-terminated poly(ethylene glycol), 4-nitrophenyl carbonate poly(ethylene glycol), chlorosilane-terminated poly(ethylene glycol), alkyl orthosilicate-terminated poly(ethylene glycol), and isocyanate-terminated poly(ethylene glycol).

In one example, the activated poly(monochloro-p-xylylene) coating is treated with 4,4'-methylenebis(phenyl isocyanate) (a diisocyanate bifunctional linker) as shown in Equation 4 below:

Equation 4:

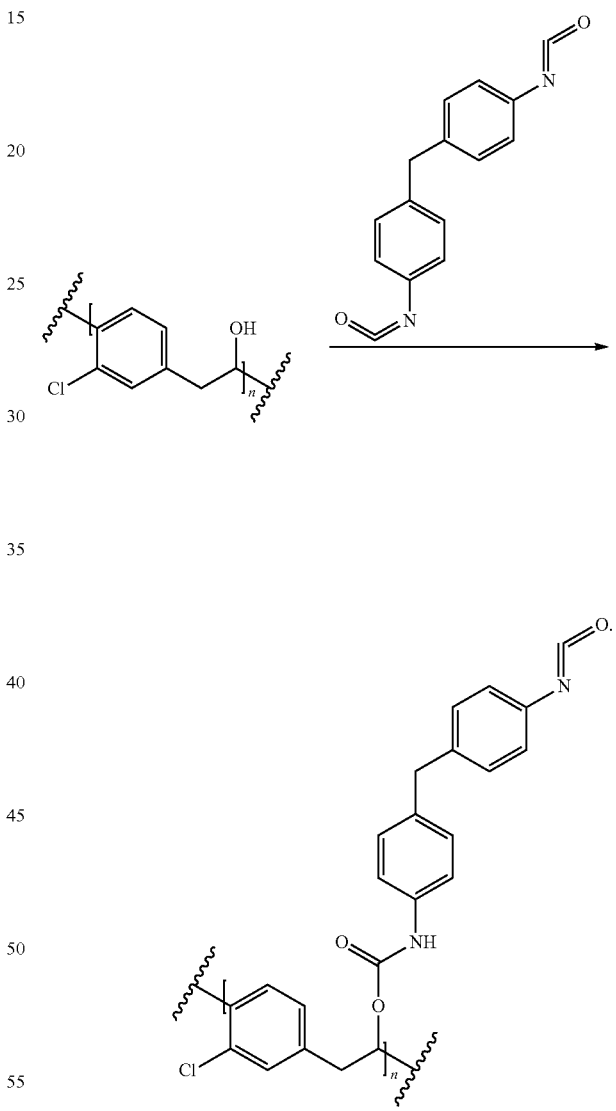

The result is a monolayer of 4,4'-methylenebis(phenyl isocyanate) covalently bonded to the poly(monochloro-p-xylylene) coating by a carbamate linkage. Following the formation of the monolayer of 4,4'-methylenebis(phenyl isocyanate), the 4,4'-methylenebis(phenyl isocyanate) monolayer may be treated with pol(ethylene glycol) or a poly(ethylene glycol) derivative, such as poly(ethylene glycol) methyl ether as shown in Equation 5 below:

Equation 5:

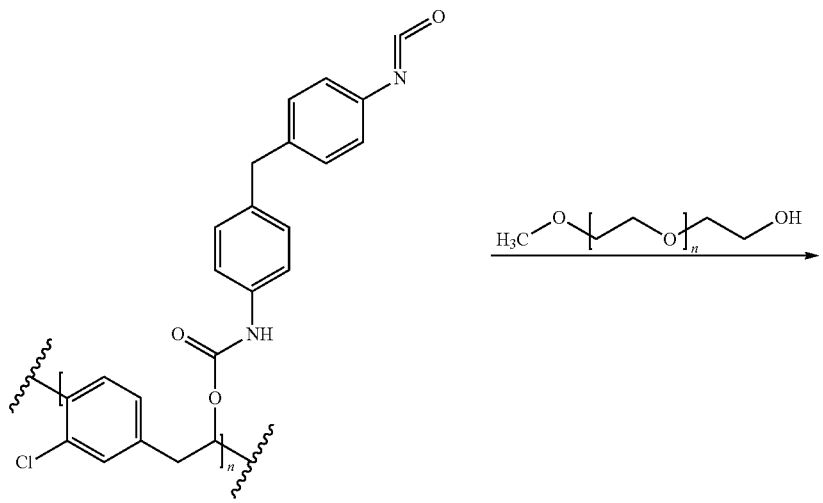

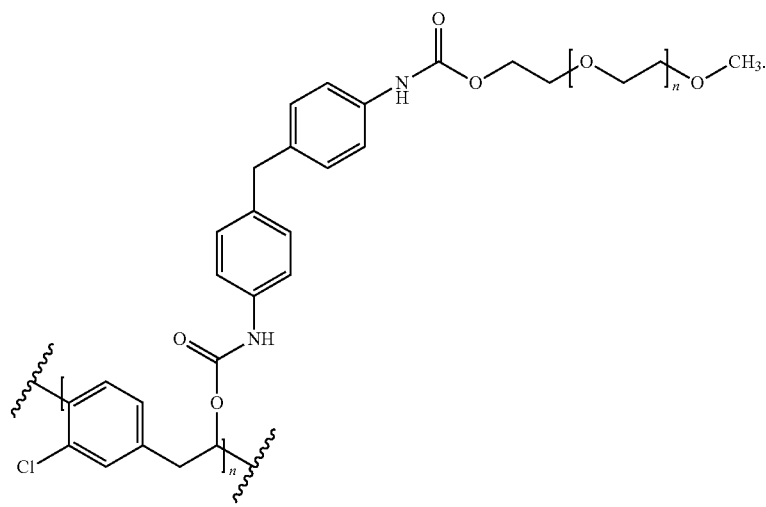

The result is a monolayer of poly(ethylene glycol) methyl ether covalently bonded to the 4,4'-methylenebis(phenyl isocyanate) monolayer by another carbamate linkage. The poly(ethylene glycol) methyl ether monolayer is durable because it is linked to the poly(monochloro-p-xylylene) coating by covalent bonds (i.e., the two carbamate linkages.) The poly(ethylene glycol) methyl ether monolayer resists cracking or peeling from the poly(monochloro-p-xylylene) coating. The resulting coating provides a reliably biologically inert surface for the implantable medical device.

In another example, the activated poly(monochloro-p-xylylene) coating is treated with (3-glycidyloxypropyl) trimethoxysilane, as shown in Equation 6 below:

Equation 6:

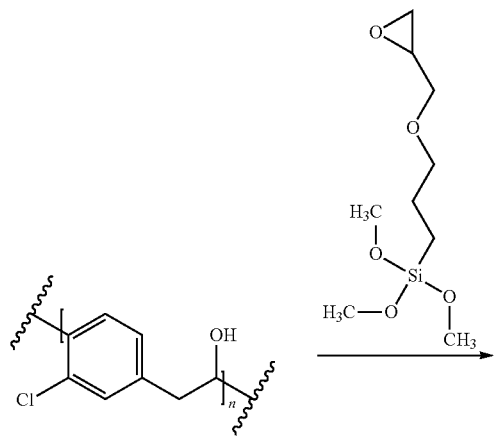

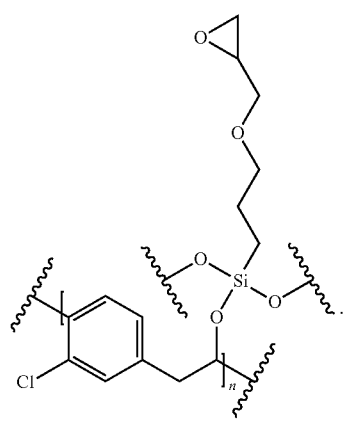

The result is a monolayer of (3-glycidyloxypropyl) trimethoxysilane covalently bonded to the poly(monochloro-p-xylylene) coating by an ether linkage. Following the formation of the monolayer of (3-glycidyloxypropyl) trimethoxysilane, the (3-glycidyloxypropyl)trimethoxysilane monolayer may be treated with pol(ethylene glycol) or a poly(ethylene glycol) derivative, such as poly(ethylene glycol) methyl ether as shown in Equation 7 below:

Equation 7:

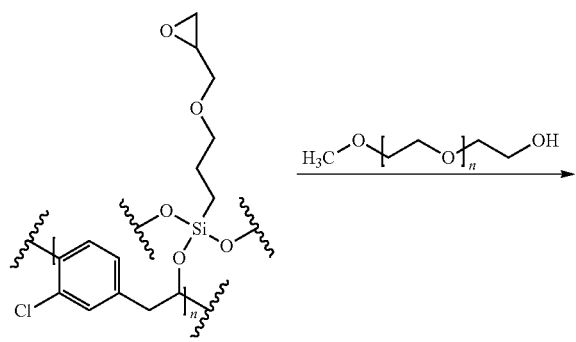

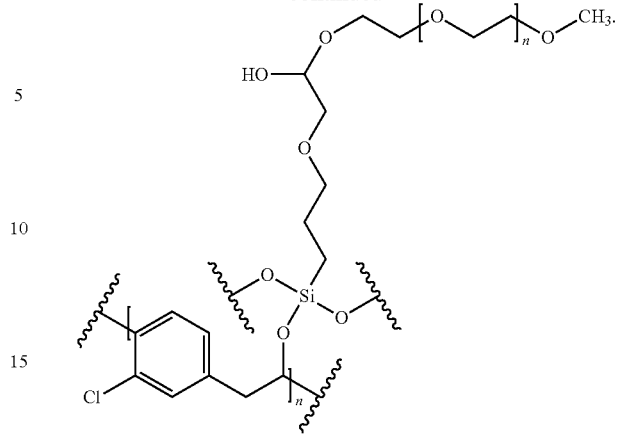

The result is a monolayer of poly(ethylene glycol) methyl ether covalently bonded to the (3-glycidyloxypropyl) trimethoxysilane monolayer by another ether linkage. The poly(ethylene glycol) methyl ether monolayer is durable and immobilized because it is linked to the poly(monochloro-p-xylylene) coating by covalent bonds (i.e., the two ether linkages.) The poly(ethylene glycol) methyl ether monolayer resists cracking or peeling from the poly(monochloro-p-xylylene) coating. The resulting coating provides a reliably biologically inert surface for the implantable medical device.

Generally, the poly(ethylene glycol) or the poly(ethylene glycol) derivatives having longer polymer chains, as indicated by higher average molecular weights, tend to impart a greater degree of durability and reliability in being biologically inert. In some embodiments, the average molecular weight of the poly(ethylene glycol) or the poly(ethylene glycol) derivative may be as little as about 200 g/mole, about 400 g/mole, about 1,000 g/mole, about 2,000 g/mole, about 4,000 g/mole, or about 6,000 g/mole, or as great as, about 10,000 g/mole, about 12,000 g/mole, about 14,000 g/mole, about 16,000 g/mole, about 18,000 g/mole, or about 20,000 g/mole, or an average molecular weight within any range defined between any pair of the foregoing values. In exemplary embodiments, the poly(ethylene glycol) or the poly (ethylene glycol) derivatives may have an average molecular weight from about 200 to 20,000 g/mole, about 400 to about 18,000 g/mole, about 1,000 to about 16,000 g/mole, about 2,000 to about 14,000 g/mole, about 4,000 to about 12,000 g/mole, or about 6,000 to about 10,000 g/mole. In some embodiments, the poly(ethylene glycol) or the poly(ethylene glycol) derivatives may have an average molecular weight of about 8,000 g/mole.

The coating embodiments described above may be incorporated into medical devices which can be implanted or inserted into the body of a patient. Example medical devices may include, without limitation, vascular grafts, electrical leads, catheters, leadless cardiac pacemakers (LCP), pelvic floor repair support devices, shock coil coverings, covered stents including for intestine, esophageal and airway applications, urethral stents, internal feeding tube/balloon, embolics/bulking agents including mitral valve repair, structural heart applications including PFO, valve leaflets, and left atrial appendage, suture sleeves, breast implants, ophthalmic applications including intraocular lenses and glaucoma tubes, and spinal disc repair. Example electrical leads may include, without limitation, implantable electrical stimulation or diagnostic systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

EXAMPLES

The present invention is more particularly described in the following examples that are intended as illustrations only, since numerous modifications and variations within the scope of the present invention will be apparent to those of skill in the art.

Example 1

Bacterial Adhesion Resistance

Bacterial adhesion resistance of titanium surfaces coated with a layer of Parylene C and a monolayer of poly(ethylene glycol) covalently bonded to Parylene C layer by an ether linkage was evaluated. Bacterial adhesion resistance is a useful demonstration of the ability of a surface to limit interaction with tissue ingrowth and resist protein adsorption. Twelve samples of titanium were prepared by cleaning with isopropyl alcohol and treated with an oxygen plasma for 5 minutes at power of 200 watts and a pressure of 250 mTorr. The cleaned samples were treated with an adhesion promoter by soaking for 10 minutes in a 5% solution of 3-(trimethoxysilyl)propyl methacrylate in a solvent mixture consisting of 50 vol. % isopropyl alcohol and 50 vol. % deionized water. The samples were rinsed in isopropyl alcohol and baked for 30 minutes at 47 degrees Celsius in ambient air. Six of the baked samples were coated with a layer of poly(monochloro-p-xylylene) having a thickness of about 10 microns. Two of the samples not coated with poly(monochloro-p-xylylene) received no further preparation (designated Ti Control). Two of the samples coated with poly(monochloro-p-xylylene) received no further preparation (designated Ti/Parylene).

The remaining eight samples (i.e., four samples not coated with poly(monochloro-p-xylylene) and four samples coated with poly(monochloro-p-xylylene)) were treated with an oxygen plasma for 60 seconds at power of 200 watts and a pressure of 250 mTorr. Four of the oxygen plasma treated samples, two samples not coated with poly(monochloro-p-xylylene) (designated Ti/PEG 400) and two samples coated with poly(monochloro-p-xylylene) (designated Ti/Parylene+PEG 400), were dipped for 15 seconds in polyethylene glycol having an average molecular weight of 400 grams/mole (PEG 400), and then rinsed with deionized water to remove polyethylene glycol not covalently bonded to the poly(monochloro-p-xylylene). The Ti/PEG 400 and Ti/Parylene+PEG 400 samples were dried by blowing them off with clean, compressed air. The remaining four oxygen plasma treated samples, two samples not coated with poly (monochloro-p-xylylene) (designated Ti/PEG 3350) and two samples coated with poly(monochloro-p-xylylene) (designated Ti/Parylene+PEG 3350), were dipped for 15 seconds in polyethylene glycol having an average molecular weight of 3350 grams/mole (PEG 3350) that was heated to a temperature of 60 degrees Celsius to liquefy the PEG 3350, and then baked at a temperature of 130 degrees Celsius for 5 minutes to cause residual PEG 3350 to drip off.

The prepared surfaces of the twelve samples, two for each of the six designated sample groups, were subjected to a short term bacterial adhesion test. The twelve samples were exposed to $S.$ $aureus$ bacteria for about 2 hours and then rinsed to remove bacteria that were not adhered to the prepared surfaces. The exposed samples were fixed, stained, and placed in an agar plate. After about 12 hours at about 37° C., the number of colony forming units per area was determined for each sample.

The efficacy of a monolayer of poly(ethylene glycol) covalently bonded to the poly(monochloro-p-xylylene) coating by an ether linkage in reducing bacterial adhesion is shown in FIG. 1. FIG. 1 is a bar graph of relative colony forming units over a predetermined area on the twelve samples prepared as described above, with each of six bars representing the average of the two samples. Greater resistance to bacterial resistance is indicated by fewer colony forming units. As shown in FIG. 1, all coated samples showed significant reductions in colony forming units, and thus, bacterial adhesion, when compared to the uncoated Titanium samples (Ti Control). Samples prepared with a monolayer of poly(ethylene glycol) covalently bonded to the poly(monochloro-p-xylylene) coating by an ether linkage (Ti/Parylene+400 PEG and Ti/Parylene+3350 PEG) showed a significant and acceptable reduction in colony forming units when compared to samples coated with a poly(monochloro-p-xylylene) coating alone or a poly(ethylene glycol) coating alone.

Example 2

Platelet Adhesion Resistance

Platelet adhesion resistance of an electropolished stainless surface coated with a layer of Parylene C and a monolayer of poly(ethylene glycol) covalently bonded to Parylene C layer by an ether linkage was evaluated. Fifteen test samples of electropolished stainless steel were prepared by cleaning with isopropyl alcohol and treated with an oxygen plasma for 5 minutes at power of 200 watts and a pressure of 250 mTorr. The cleaned test samples were treated with an adhesion promoter by soaking for 10 minutes in a 5% solution of 3-(trimethoxysilyl)propyl methacrylate in a solvent mixture consisting of 50 vol. % isopropyl alcohol and 50 vol. % deionized water. The test samples were rinsed in isopropyl alcohol and baked for 30 minutes at 47 degrees Celsius in ambient air. The baked test samples were coated with a layer of poly(monochloro-p-xylylene) having a thickness of about 10 microns. Five of the coated test samples received no further preparation (designated SS/Parylene)

The ten remaining poly(monochloro-p-xylylene) coated test samples were treated with an oxygen plasma at power of 200 watts and a pressure of 250 mTorr, five test samples for 1 minute (designated SS/Parylene+1 min+PEG), and five test samples for 5 minutes (designated SS/Parylene+5 min+ PEG). The ten oxygen plasma treated test samples were dipped for 15 seconds in polyethylene glycol having an average molecular weight of 3350 grams/mole (PEG 3350) that was heated to a temperature of 60 degrees Celsius to liquefy the PEG 3350, and then baked at a temperature of 130 degrees Celsius to cause residual PEG 3350 to drip off.

The fifteen test samples, along with five electropolished stainless steel samples (designated Negative Control) and five electropolished gold samples (designated Positive Control) were soaked in a phosphate buffered saline solution at room temperature for 10 minutes and dried by capillary wicking. The twenty-five samples (five designated groups of five samples each) were placed into a Diamed Impact-R platelet adhesion tester. Citrated whole human blood from five donors was deposited on the twenty-five samples, with blood from each donor being deposited on a different sample from each of the five designated groups. The platelets in the deposited blood were activated by spinning the samples in the platelet adhesion tester for 300 seconds at 720 revolutions per minute. Each of the samples were washed four times with phosphate buffered saline to remove residual cells not adhered to the sample surface. The samples were fixed and stained with anti-CD31 antibody. Each of the samples was imaged via confocal microscopy covering three separate fields of view. A percentage platelet coverage value was determined for each field of view. An average percentage platelet coverage value was determined for each of the five designated groups and normalized as a percentage of the platelet coverage of the electropolished gold samples (designated Positive Control). The results are shown in FIG. 2.

Figure 2:
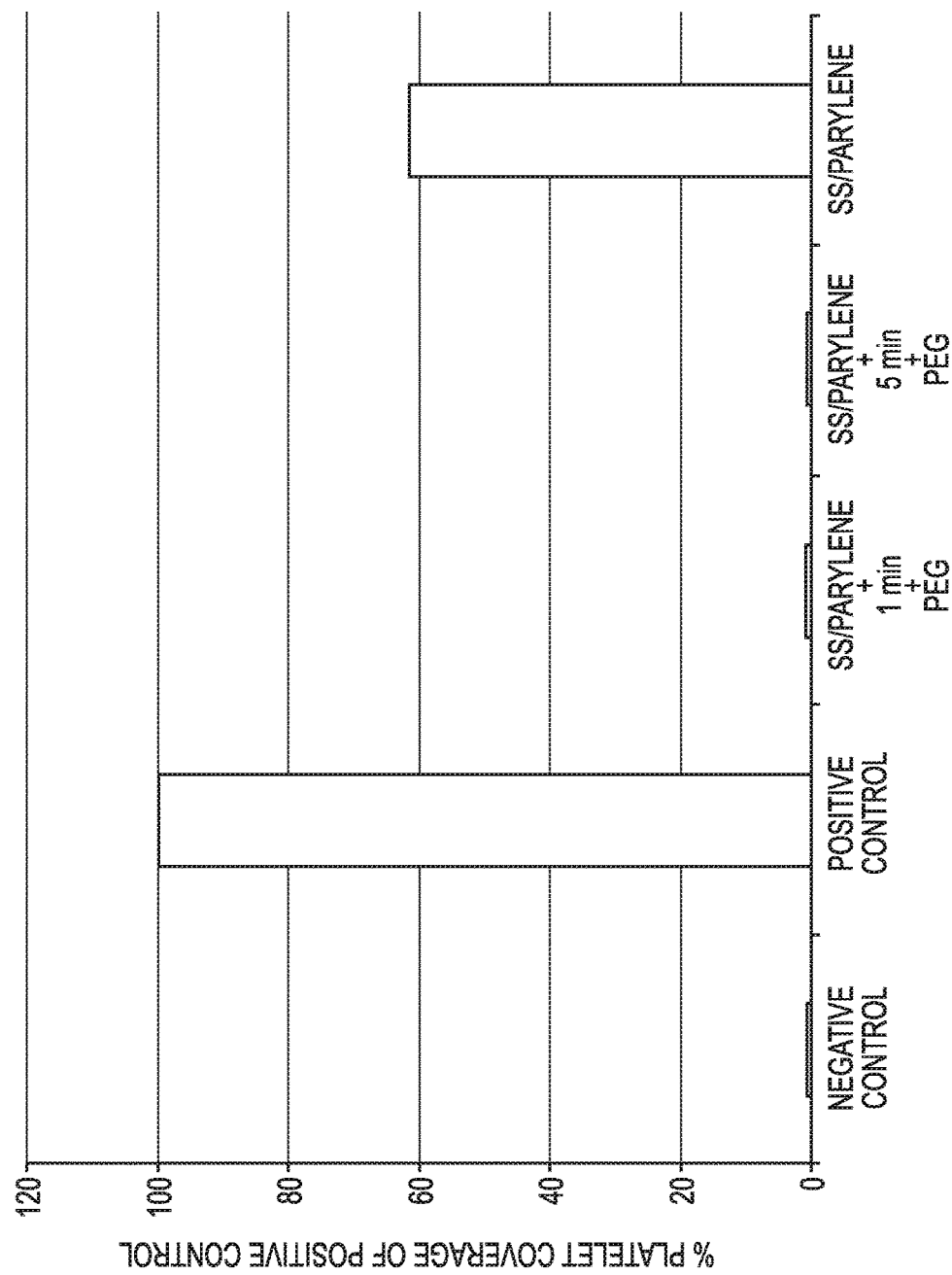
FIG. 2 is a graph of normalized platelet adhesion in accordance with embodiments of the disclosure.

The efficacy of a monolayer of poly(ethylene glycol) covalently bonded to the poly(monochloro-p-xylylene) coating by an ether linkage in reducing platelet adhesion is shown in FIG. 2. FIG. 2 is a bar graph of normalized percentage platelet coverage for each of the five designated groups, with each bar representing an average of fifteen fields of view (three per sample, five donor samples per designated group). Greater resistance to platelet adhesion indicated by a lower percentage platelet coverage. As shown in FIG. 2, the samples prepared with monolayer of poly (ethylene glycol) covalently bonded to the poly(monochloro-p-xylylene) coating by an ether linkage, SS/Parylene+1 min+PEG and SS/Parylene+5 min+PEG, showed significantly less platelet coverage, and thus less platelet adhesion, compared to samples with coated with poly(monochloro-p-xylylene) alone (SS/Parylene). The platelet coverage for the SS/Parylene+1 min+PEG and SS/Parylene+5 min+PEG samples is nearly as low as the Negative Control.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A coating for an implantable medical device, the coating comprising:
    a poly(monochloro-p-xylylene) coating formed on at least a portion of the implantable medical device;
    a monolayer including at least one of poly(ethylene glycol) and a poly(ethylene glycol) derivative linked to the poly(monochloro-p-xylylene) coating by covalent bonds; and
    a bifunctional linker disposed between the poly(monochloro-p-xylylene) coating and the monolayer including at least one of poly(ethylene glycol) and a poly(ethylene glycol) derivative, wherein the bifunctional linker is covalently bonded to the poly(monochloro-p-xylylene) coating and to the monolayer including at least one of poly(ethylene glycol) and a poly(ethylene glycol) derivative.

2. The coating of claim 1, wherein an average molecular weight of the at least one of the poly(ethylene glycol) and a poly(ethylene glycol) derivative is between about 200 grams per mole and about 20,000 grams per mole.

3. The coating of claim 1, wherein the monolayer including at least one of poly(ethylene glycol) and a poly(ethylene glycol) derivative includes poly(ethylene glycol) methyl ether.

4. The coating of claim 1, wherein the bifunctional linker includes a diisocyanate.

5. The coating of claim 1, wherein the bifunctional linker includes (3-glycidyloxypropyl)trimethoxysilane.

6. An implantable medical device comprising:
    an exterior surface; and
    a coating disposed on at least a portion of the exterior surface, the coating comprising:
        a poly(monochloro-p-xylylene) coating formed on at least a portion of the implantable medical device;
        a monolayer including at least one of poly(ethylene glycol) and a poly(ethylene glycol) derivative linked to the poly(monochloro-p-xylylene) coating by covalent bonds; and
        a bifunctional linker disposed between the poly(monochloro-p-xylylene) coating and the monolayer including at least one of poly(ethylene glycol) and a poly(ethylene glycol) derivative, wherein the bifunctional linker is covalently bonded to the poly(monochloro-p-xylylene) coating and to the monolayer including at least one of poly(ethylene glycol) and a poly(ethylene glycol) derivative.

7. A method for coating an implantable medical device, the method comprising:
    forming a coating of poly(monochloro-p-xylylene) on at least a portion of the implantable medical device;
    activating a surface of the poly(monochloro-p-xylylene) coating by forming hydroxyl groups on the surface;
    treating the activated surface with a bifunctional linker, forming a monolayer of the bifunctional linker covalently bonded to the surface; and
    treating the monolayer of the bifunctional linker with at least one of a poly(ethylene glycol) and a poly(ethylene glycol) derivative, forming a monolayer of the at least one of a poly(ethylene glycol) and a poly(ethylene glycol) derivative covalently bonded to the monolayer of the bifunctional linker.

8. The method of claim 7, wherein activating the surface of the layer of poly(monochloro-p-xylylene) includes treating the surface with an oxygen-containing plasma.

9. The method of claim 7, wherein activating the surface of the layer of poly(monochloro-p-xylylene) includes treating the surface with ultraviolet light in an oxygen-containing atmosphere.

10. The method of claim 7, wherein the at least one of a poly(ethylene glycol) and a poly(ethylene glycol) derivative includes poly(ethylene glycol).

11. The method of claim, 7, wherein the at least one of a poly(ethylene glycol) and a poly(ethylene glycol) derivative includes methoxy poly(ethylene glycol).

12. The method of claim 7, wherein the at least one of a poly(ethylene glycol) and a poly(ethylene glycol) derivative includes poly(ethylene glycol) methyl ether.

13. The method of claim 7, wherein the bifunctional linker includes a diisocyanate.

14. The method of claim 13, wherein the diisocyanate is 4,4'-methylenebis(phenyl isocyanate).

15. The method of claim 7, wherein the bifunctional linker includes (3-glycidyloxypropyl)trimethoxysilane.

* * * * *